(12) United States Patent
Koonce

(10) Patent No.: US 10,832,844 B2
(45) Date of Patent: Nov. 10, 2020

(54) DUAL PHASE MULTI-FREQUENCY ELECTROMAGNETIC GENERATOR

(71) Applicant: Gene Koonce, Greeley, CO (US)

(72) Inventor: Gene Koonce, Greeley, CO (US)

(73) Assignee: Gene Koonce, Greeley, CO (US)

( * ) Notice: Subject to any disclaimer, the term of this patent is extended or adjusted under 35 U.S.C. 154(b) by 267 days.

(21) Appl. No.: 15/877,701

(22) Filed: Jan. 23, 2018

(65) Prior Publication Data

US 2018/0233259 A1 Aug. 16, 2018

Related U.S. Application Data

(60) Provisional application No. 62/449,428, filed on Jan. 23, 2017.

(51) Int. Cl.

| | |
|---|---|
| *A61N 5/00* | (2006.01) |
| *H01F 7/06* | (2006.01) |
| *G01R 33/00* | (2006.01) |
| *H05B 41/14* | (2006.01) |
| *H01F 27/28* | (2006.01) |
| *H01F 5/00* | (2006.01) |
| *H01Q 7/00* | (2006.01) |
| *A61B 5/05* | (2006.01) |

(52) U.S. Cl.
CPC ......... *H01F 7/064* (2013.01); *G01R 33/0035* (2013.01); *H01F 5/00* (2013.01); *H01F 27/28* (2013.01); *H05B 41/14* (2013.01); *A61B 5/05* (2013.01); *H01F 2005/006* (2013.01); *H01Q 7/00* (2013.01)

(58) Field of Classification Search
None
See application file for complete search history.

(56) References Cited

U.S. PATENT DOCUMENTS

| | | | | |
|---|---|---|---|---|
| 6,217,604 B1 * | 4/2001 | Azure | ................... | A61N 2/002 600/14 |
| 6,972,115 B1 * | 12/2005 | Ballard | ................. | B01J 19/088 422/186.04 |
| 7,235,945 B2 * | 6/2007 | Correa | ................. | H02N 11/002 315/111.31 |
| 7,583,172 B2 * | 9/2009 | Koonce | ..................... | H01F 5/00 313/153 |

* cited by examiner

*Primary Examiner* — Stephen W Jackson
(74) *Attorney, Agent, or Firm* — William W. Cochran; Cochran Freund & Young LLC

(57) ABSTRACT

Disclosed is a dual phase, multi-frequency, electromagnetic generator that creates electromagnetic fields having a first phase on a first side of said electromagnetic generator and electromagnetic fields having a second phase on an opposite side of said electromagnetic generator. In addition, gaseous emission tubes generate light frequency signals on each side of the electromagnetic generator. Tesla coils are disposed at least partially within the cone of a conically shaped transmission coil to achieve a high degree of coupling between the conically shaped transmission coils and the Tesla coils. Sparks gaps are used to create a fast rise time signal, which creates multiple frequencies.

4 Claims, 6 Drawing Sheets

DUAL PHASE MULTI-FREQUENCY ELECTROMAGNETIC GENERATOR

BACKGROUND OF THE INVENTION

Various types of electromagnetic field generators have existed for some time. For example, U.S. Pat. Nos. 6,933,819 and 7,583,172 describe electromagnetic field generators that are capable of generating multiple frequencies. These patents are specifically incorporated herein by reference for all that they disclose and teach. Multi-frequency electromagnetic generators can be used for various purposes, including use as energy transfer devices. For example, multi-frequency electromagnetic generators can be used to transfer energy to living tissue. Electromagnetic field generators can also be used for testing and calibration of flux meters, including flux meters capable of detecting multiple frequencies.

SUMMARY OF THE INVENTION

The present invention may therefore comprise a method of generating dual phase, multi-frequency electromagnetic fields comprising: applying an AC input signal to a primary coil of a center tapped transformer; connecting a first secondary coil to a first charging capacitor and a first spark gap; connecting a first conically shaped, spiral transmission coil to the first spark gap so that the first conically shaped, spiral transmission coil generates a first multi-frequency spiral, conically shaped electromagnetic field; placing a first Tesla coil at least partially in the first multi-frequency, spiral, conically shaped electromagnetic field so that the first multi-frequency, spiral, conically shaped electromagnetic field induces a first current in the first Tesla coil; transmitting the first current to a first antenna to create a first multi-frequency electromagnetic field having a first predetermined phase.

An embodiment of the present invention may further comprise a dual phase, multi-frequency, electromagnetic generator comprising: a center tap transformer that is coupled to an alternating current input that creates a first charging signal from a first secondary coil of the center tap transformer, and creates a second charging signal from a second secondary coil of the center tap transformer; a first charging capacitor that is connected to the first secondary coil that accumulates a first charge from the first charging signal; a second charging capacitor that is connected to the second secondary coil that accumulates a second charge from the second charging signal; a first spark gap that discharges when the first charging capacitor reaches a first predetermined voltage; a second spark gap that discharges when the second charging capacitor reaches a second predetermined voltage; a first conically shaped transmission coil attached to the first spark gap that generates a first multi-frequency transmission having a first phase; a second conically shaped transmission coil attached to the second spark gap that generates a second multi-frequency signal having a second phase that is 180 degrees different from the first phase; a first Tesla coil that is at least partially disposed in the first conically shaped transmission coil that receives the first multi-frequency transmission which induces a first current in the first Tesla coil; a second Tesla coil that is at least partially disposed in the second conically shaped transmission coil that receives the second multi-frequency transmission which induces a second current in the second Tesla coil; a first antenna that transmits a first electromagnetic field in response to the first current induced in the first Tesla coil; a second antenna that transmits a second electromagnetic field signal in response to the second current induced in the second Tesla coil.

DETAILED DESCRIPTION OF THE EMBODIMENTS

Figure 1:
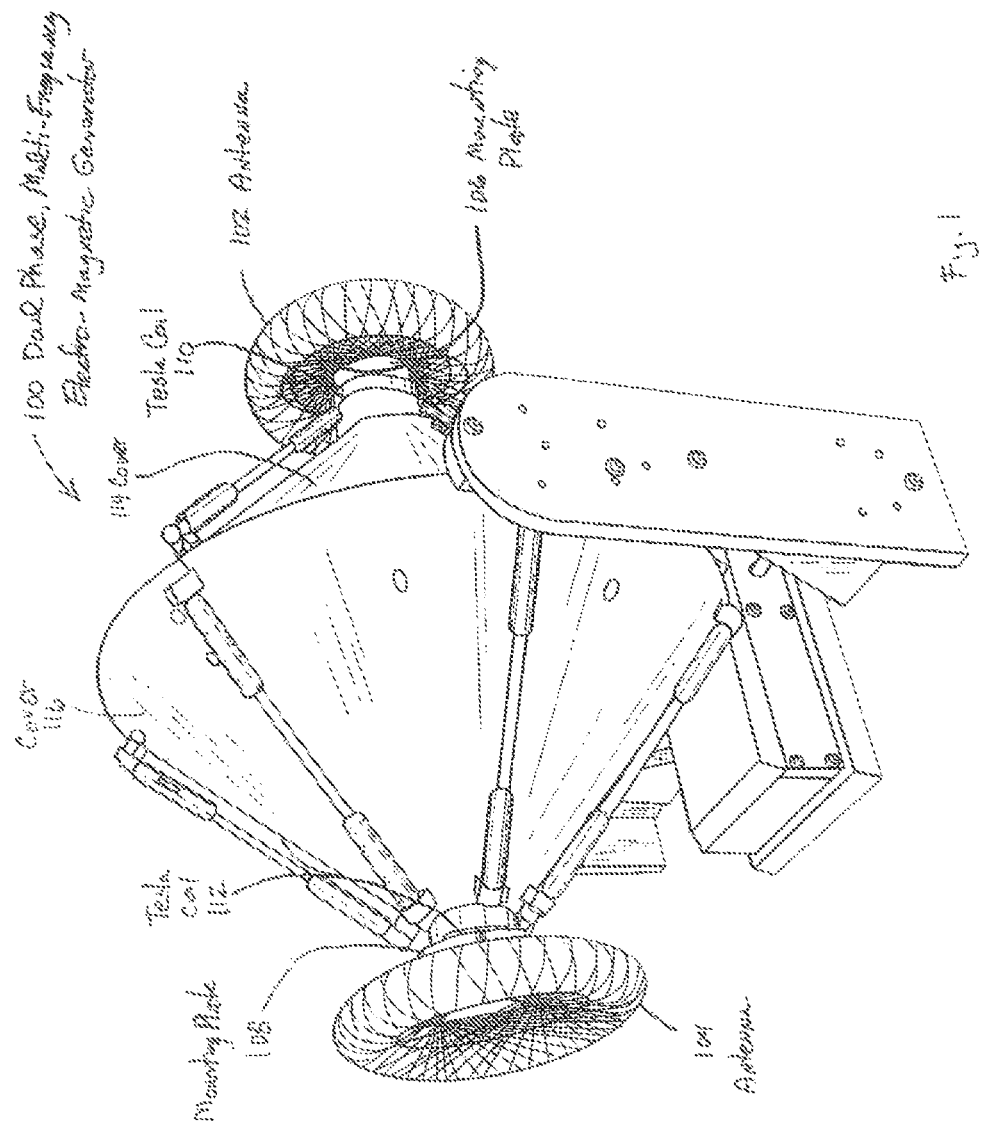
FIG. 1 is perspective view of the dual phase, multi-frequency electromagnetic generator.

FIG. 1 is an isometric view of the dual phase, multi-frequency electromagnetic generator 100. As illustrated in FIG. 1, the dual phase multi-frequency electromagnetic generator 100 has two antennas 102, 104 that are mounted on opposite sides of the dual phase multi-frequency electromagnetic generator 100. The antennas 102, 104 generate electromagnetic fields that have opposite phases of operation. Antennas 102, 104 are mounted on mounting plates 106, 108, respectively. Tesla coils 110, 112 extend through the mounting plates 106, 108, as well as covers 114, 116. Covers 114, 116 may be constructed from Lexan or other plastic that allows the transmission of electromagnetic fields.

Figure 2:
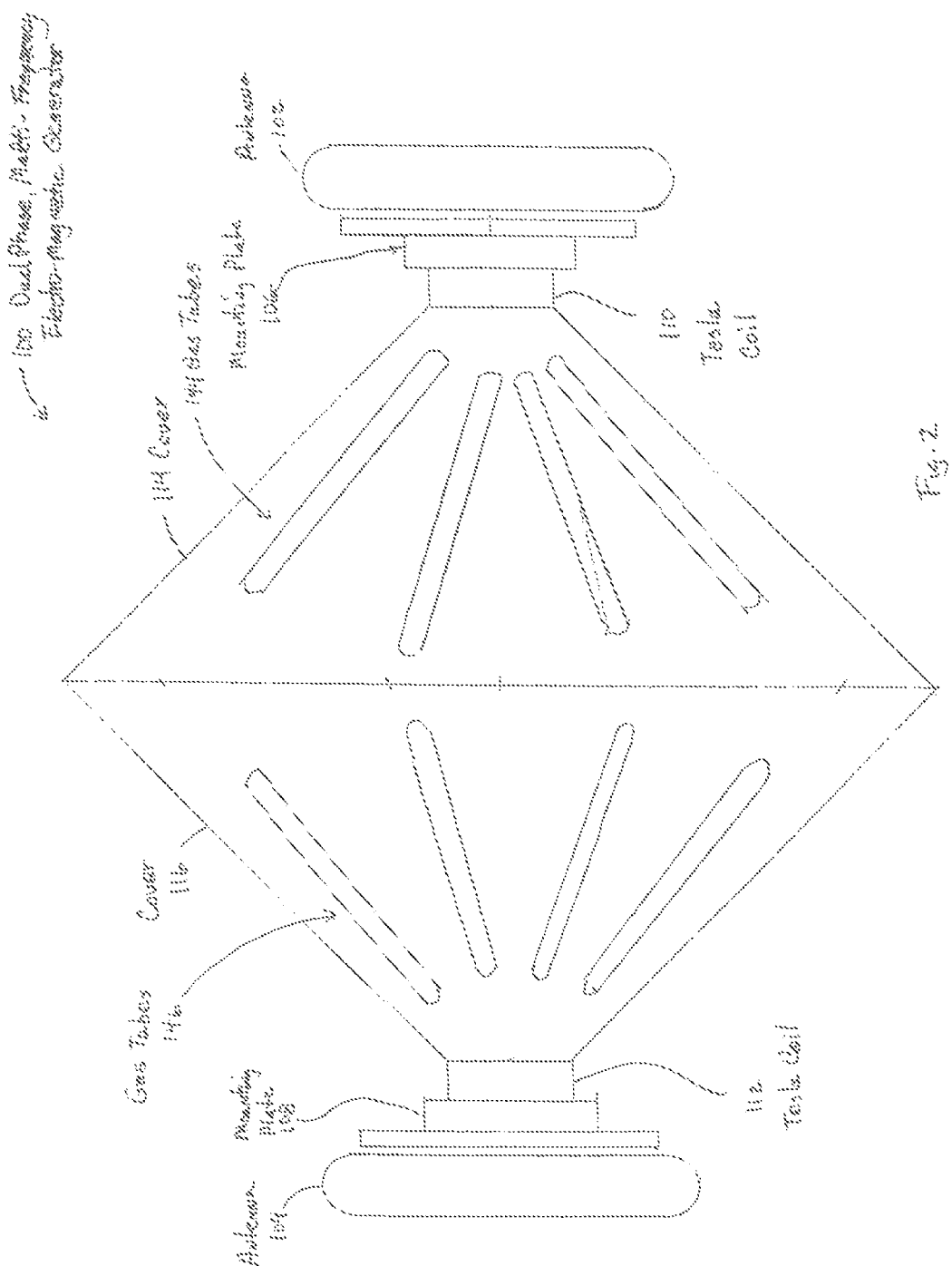
FIG. 2 is a side view of the dual phase, multi-frequency electromagnetic generator of FIG. 1.

FIG. 2 is a side view of the dual phase, multi-frequency electromagnetic generator 100. As illustrated in FIG. 2, antennas 102, 104 are shown on opposite sides of the covers 114, 116. Mounting plate 106 supports the Tesla coil 110 which extends inwardly through the cover 114. Similarly, mounting plate 108 supports the Tesla coil 112, which extends inwardly through the cover 116.

Figure 3:
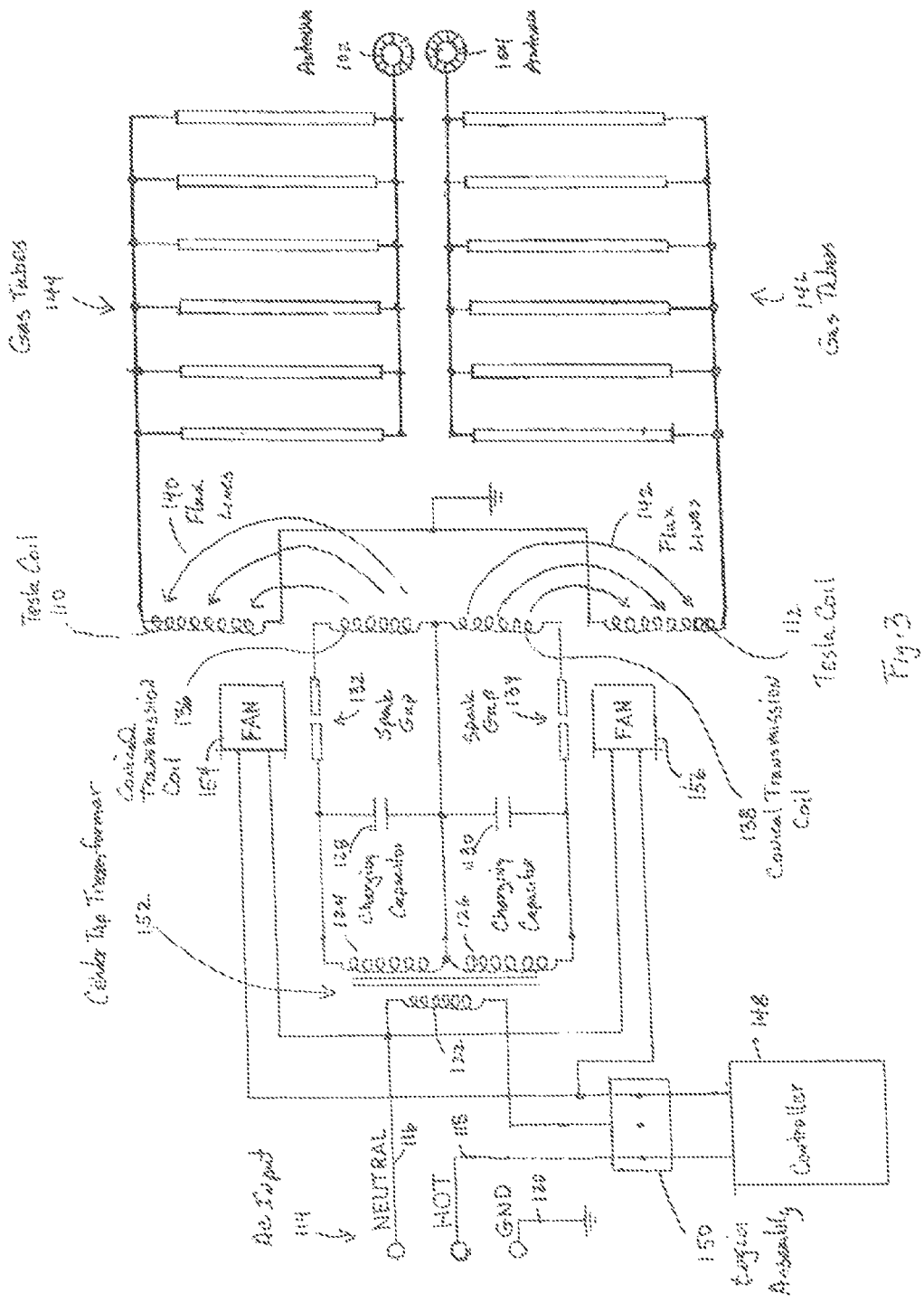
FIG. 3 is a schematic circuit diagram of the dual phase, multi-frequency electromagnetic generator of FIG. 1.

FIG. 3 is a schematic circuit diagram illustrating the electrical components of the dual phase, multi-frequency electromagnetic generator. As illustrated in FIG. 3, an alternating current input 114 is applied to the neutral terminal 116, hot terminal 118 and ground terminal 120. The neutral input 116 is connected to the primary coil of center tap transformer 152. The opposite end of the primary coil 122 is connected to logic assembly 150. The hot terminal 118 is also connected to the logic assembly 150. Fans 154, 156 are also connected to logic assembly 150. The logic assembly 150 is connected to the controller 148. The controller 148 controls the logic assembly 150, which is capable of turning the fans 154, 156 on and off and also controls the AC input 114 to the center tap transformer 152. The controller 148, for example, may provide a delayed start or may cycle the operation of the dual phase, multi-frequency electromagnetic generator 100 by controlling the application of current to the primary coil 122.

The primary coil 122 of the center tap transformer 152, illustrated in FIG. 3, drives the secondary coils 124, 126 of the center tap transformer 152. The primary coil 122 induces current in both the secondary coil 124 and secondary coil 126. The current induced in the secondary coil 126 has the opposite phase of the current that is induced in secondary coil 124. In other words, the current flowing through the secondary coils 124, 126 is 180 degrees out of phase. As the voltage increases on the secondary coil 124, the capacitor 128 is charged until the voltage on the charging capacitor 128 is sufficiently high to cause the spark gap 132 to discharge. When the spark gap 132 discharges, a pulse is transmitted to the conical transmission coil 136. The conical transmission coil 136 generates multi-frequency electromagnetic transmissions that create flux lines 140 that are received by Tesla coil 110. The electromagnetic energy of the flux lines 140 creates a current in the Tesla coil 110 that is then transmitted to the gas tubes 144. Gas tubes 144 generate electromagnetic light frequency energy. The opposite ends of the gas tubes 144 are connected together and connected to antenna 102, which transmits an electromagnetic signal in response to the electrical signal transmitted through the gas tubes 144. Because of the fast rise time of the pulse created by the spark gap 132, multiple frequencies are generated by the conical transmission coil 136. Because of the placement of the Tesla coil 110 and the conical shape of the spiral conical transmitting coil 136, a high degree of coupling is achieved between the conical transmitting coil 136 and the Tesla coil 110.

Similarly, as the voltage in the secondary coil 126 increases, the voltage on the charging capacitor 130 increases until a sufficient amount of voltage is stored on capacitor 130 to cause the spark gap 134 to discharge. This causes a fast rise time signal to be applied to the conical transmission coil 138. The fast rise time of the pulse that is applied to the conical transmitting coil 138 creates a multiple frequency electromagnetic signal having flux lines 142. Flux lines 142 couple to the Tesla coil 112, which induces a signal in the Tesla coil 112. The multi-frequency signal that is induced in the Tesla coil 112 is applied to gas tubes 146, which irradiate light frequency signals in various light spectra. The multiple frequency signal that is transmitted through the gas tubes 146 is then applied to antenna 104, which generates a multi-frequency electromagnetic signal that is transmitted by the antenna 104. Fans 152, 154 provide cooling for the spark gaps 132, 134, respectively.

As is readily apparent from the schematic circuit diagram of FIG. 3, the top portion of the circuit diagram of FIG. 3 has a first phase, while the lower portion of the circuit diagram of FIG. 3 has an opposite phase, or a phase that is 180 degrees different from the phase of the signal in the top circuit. Accordingly, flux lines 140 and flux lines 142 are generated 180 degrees out of phase, which causes the gas tubes 144, 146 to be 180 degrees out of phase and the electromagnetic signal on antennas 102, 104 to be 180 degrees out of phase. Since the antennas 102, 104 and gas tubes 144, 146, as well as the conical transmission coils 136, 138, and Tesla coils 110, 112, are located on opposite sides of the dual phase, multi-frequency electromagnetic generator, electromagnetic signals are generated 180 degrees out of phase from each side of the dual phase, multi-frequency electromagnetic generator 100. This out of phase transmission of signals from side to side of the dual phase multi-frequency electromagnetic generator 100, illustrated in FIG. 2, provides a unique effect with regard to the spatial generation of multi-frequency electromagnetic energy at both light frequencies and radiowave frequencies. The temporal and spatial separation of these fields provides a unique energy distribution pattern.

Figure 4:
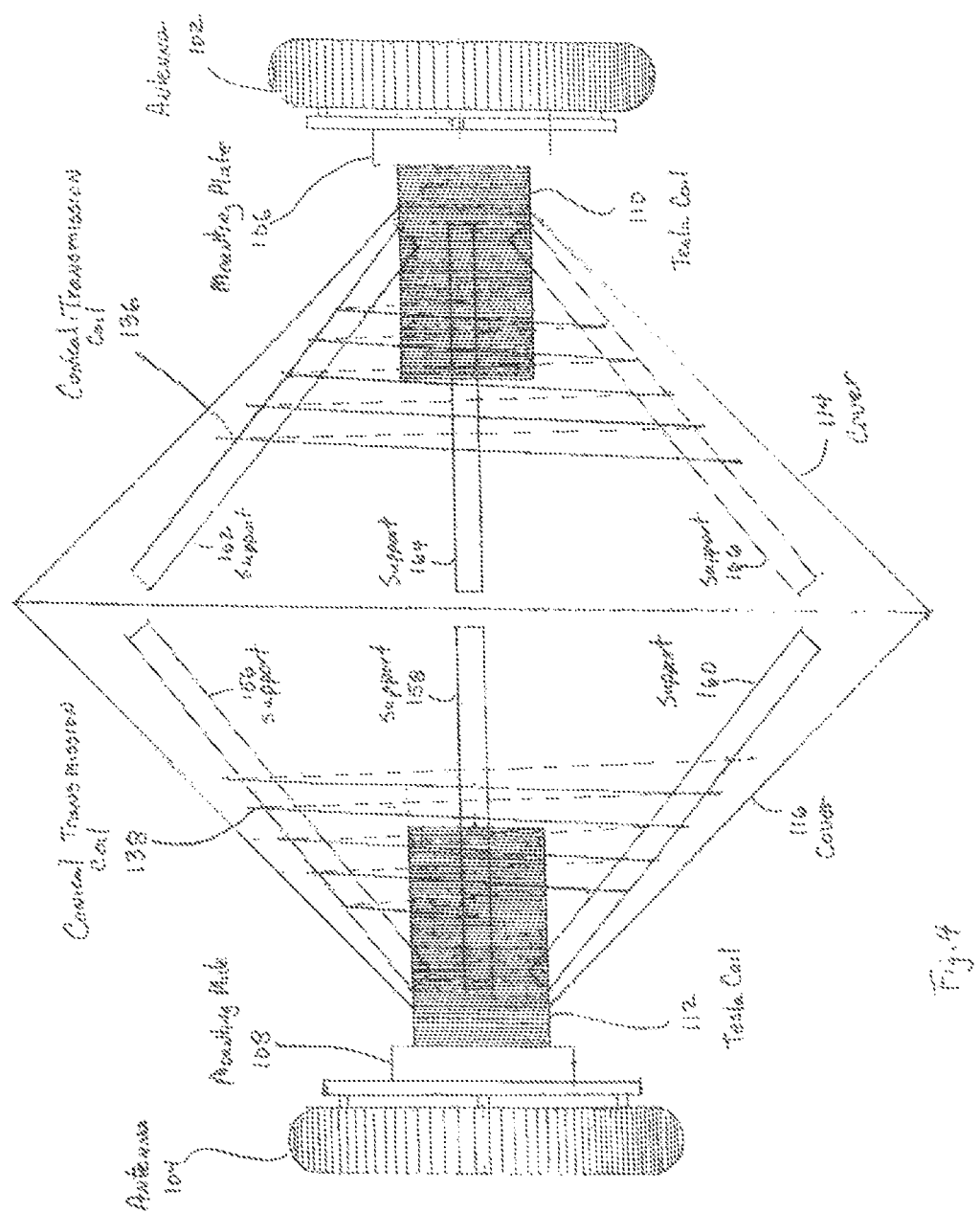
FIG. 4 is a side view of certain components of the dual phase multi-frequency electromagnetic generator of FIG. 1.

FIG. 4 is a schematic transparent side view of the dual phase multi-frequency electromagnetic generator 100, illustrating a number of the component parts. As illustrated in FIG. 4, antennas 102, 104 are disposed on each end of the generator 100. Tesla coils 110, 112 are mounted to mounting plates 106, 108, respectively. The Tesla coils 110, 112 extend into the covers 114, 116, respectively. Conical transmitting coil 136 is supported by supports 102, 104, 106. The conical transmission coil 136 is a spiral coil of conductive material that extends around at least a portion of Tesla coil 110. The conical transmission coil 136 can be an antenna wire or copper tubing. Similarly, conical transmission coil 138 is supported by supports 156, 158, 160. The conical transmission coil 138 is a spiral that is formed in a conical shape that extends around Tesla coil 112. The conical shape of the conical transmission coils 130, 136 provides a high degree of electromagnetic coupling between the conical transmission coils 136, 138 and the Tesla coils 110, 112. This is because of the fact that the conical transmission coils 136 extend around at least a portion of the Tesla coils 110, 112, respectively, and the angle of the coils produces electromagnetic fields that couple easily and directly onto the coils of the Tesla coils 110, 112. In this case, the Tesla coils 110, 112 function as antennas and current is induced in the Tesla coils 110, 112 by the electromagnetic fields that are created by the conical transmission coils 136, 138, respectively. In this manner, an effective transfer of energy from the conical transmission coils 136, 138 to the Tesla coils 110, 112 is achieved.

Figure 5:
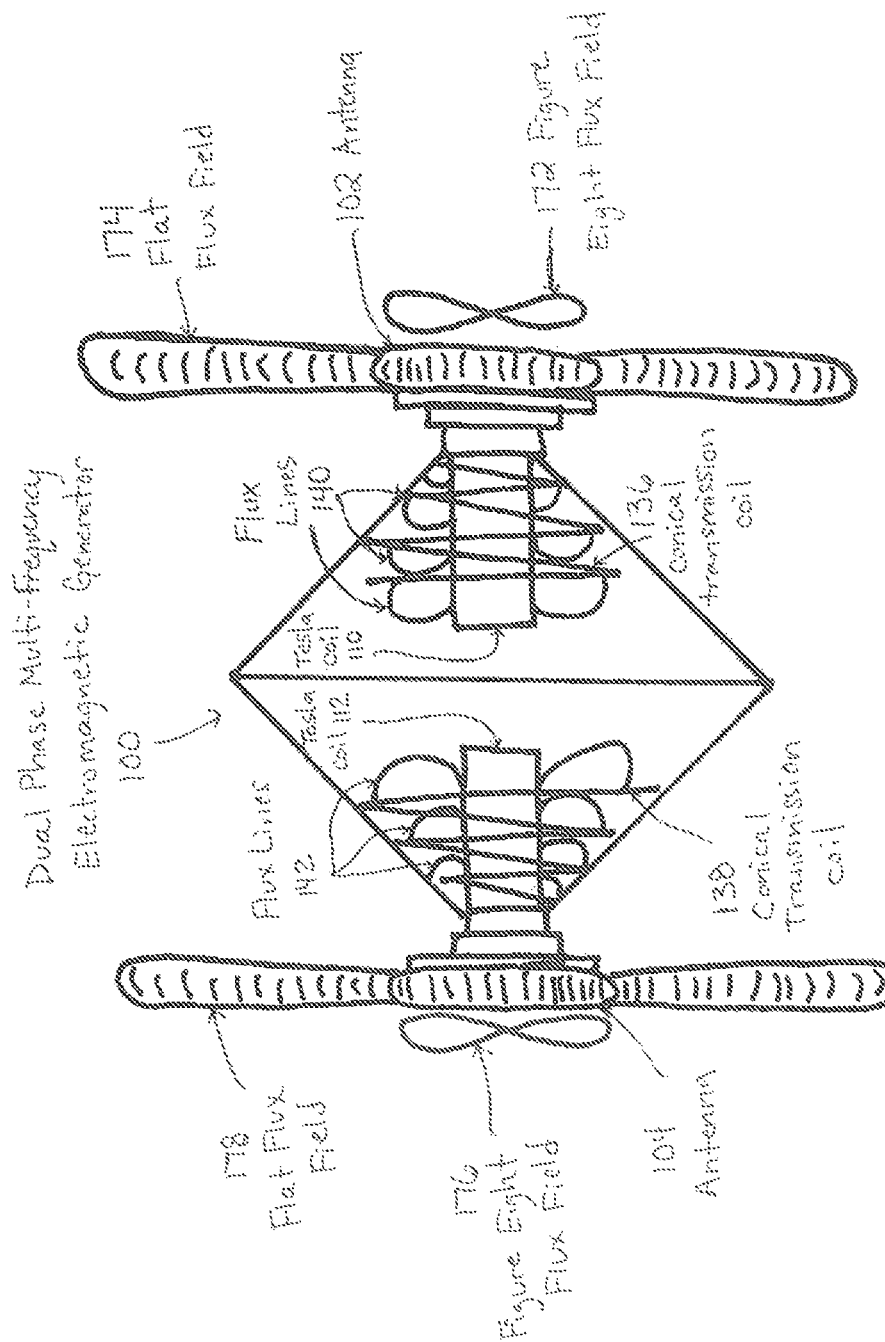
FIG. 5 is a side view of the dual phase multi-frequency electromagnetic generator of FIG. 1 showing flux lines of various fields generated by the dual phase multi-frequency electromagnetic generator.

FIG. 5 is a schematic representation of the magnetic fields that are created by the dual phase multi-frequency electromagnetic generator 100. The fields are illustrated for the purpose of showing general shapes, but are not to scale and the fields typically extend well beyond that which is shown in FIG. 5. As illustrated in FIG. 5, antenna 102 creates a figure eight flux field 172 that projects outwardly in a horizontal direction, as illustrated in FIG. 5, and a flat flux field 174 that projects outwardly from the antenna and surrounds the antenna in a circular field. The conical transmission coil 136 generates flux fields 140 that are coupled to the Tesla coil 110. Similarly, conical transmission coil 138 creates flux lines 142 that are coupled to the Tesla, coil 112. Antenna 104 generates a figure eight flux field 176 that projects outwardly in a horizontal direction to the left, as illustrated in FIG. 5. Antenna 104 also creates a flat flux field 178 that has a circular shape around the antenna 104.

Figure 6:
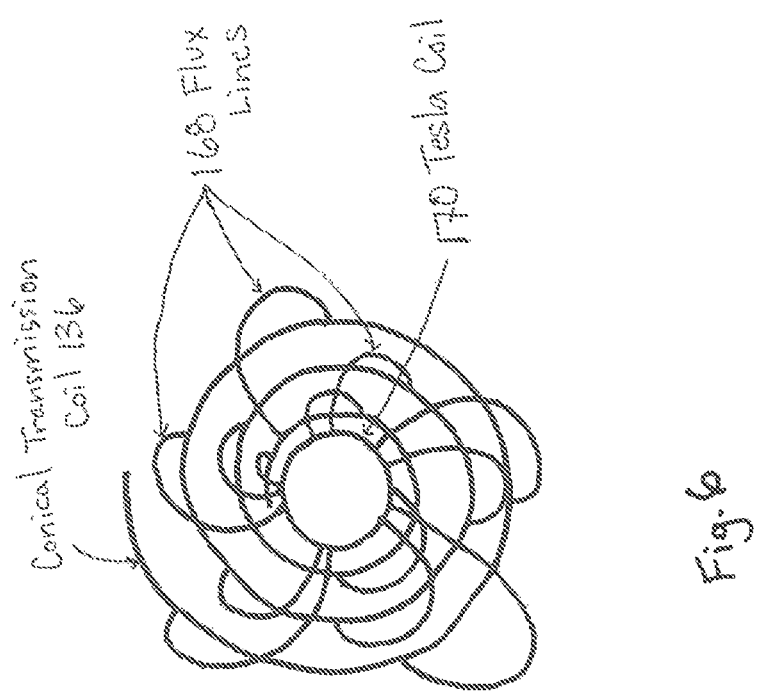
FIG. 6 is an end view of conical transmission coil 136 illustrating fax lines generated by the conical transmission coil 136.

FIG. 6 is an end side view of the conical transmission coil 136 with the Tesla 170 disposed in a center position around the conical transmission coil 136. FIG. 6 illustrates the various flux lines 168 that couple the electromagnetic energy from the conical transmission coil 136 to the Tesla coil 170 in an efficient manner.

The embodiments of the present invention therefore provide an electromagnetic generator that creates light frequency electromagnetic energy, as well as radio frequency electromagnetic energy that has multiple frequencies. The use of a center tap transformer allows for the transmission of electromagnetic energy in opposite phases at each end of the dual phase multi-frequency electromagnetic generator 100. As such, unique electromagnetic fields, as well as unique light energy is created by the dual phase multi-frequency electromagnetic generator 100.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A method of generating dual phase, multi-frequency electromagnetic fields comprising:
    applying an AC input signal to a primary coil of a center tapped transformer; connecting a first secondary coil to a first charging capacitor and a first spark gap; connecting a first conically shaped, spiral transmission coil to said first spark gap so that said first conically shaped, spiral transmission coil generates a first multi-frequency spiral, conically shaped electromagnetic field;
    placing a first Tesla coil at least partially in said first multi-frequency, spiral, conically shaped electromagnetic field so that said first multi-frequency, spiral, conically shaped electromagnetic field induces a first current in said first Tesla coil;
    transmitting said first current to a first antenna to create a first multi-frequency electromagnetic field having a first predetermined phase
    connecting a second secondary coil to a second charging capacitor and a second spark gap;
    connecting said second conically shaped, spiral transmission coil to said second spark gap so that said second conically shaped, spiral transmission coil generates said second multi-frequency spiral, conically shaped electromagnetic field;
    placing a second Tesla coil at least partially in said spiral, conically shaped electromagnetic field so that said second spiral, conically shaped electromagnetic field induces a second current in said second Tesla coil;
    transmitting said second current to a second antenna to create a second multi-frequency electromagnetic field having a second predetermined phase that is 180 degrees different from said first multi-frequency electromagnetic field.

2. A dual phase, multi-frequency, electromagnetic generator comprising:
    a center tap transformer that is coupled to an alternating current input that creates a first charging signal from a first secondary coil of said center tap transformer, and creates a second charging signal from a second secondary coil of said center tap transformer;
    a first charging capacitor that is connected to said first secondary coil that accumulates a first charge from said first charging signal;
    a second charging capacitor that is connected to said second secondary coil that accumulates a second charge from said second charging signal;
    a first spark gap that discharges when said first charging capacitor reaches a first predetermined voltage;
    a second spark gap that discharges when said second charging capacitor reaches a second predetermined voltage;
    a first conically shaped transmission coil attached to said first spark gap that generates a first multi-frequency transmission having a first phase;
    a second conically shaped transmission coil attached to said second spark gap that generates a second multi-frequency signal having a second phase that is 180 degrees different from said first phase;
    a first Tesla coil that is at least partially disposed in said first conically shaped transmission coil that receives said first multi-frequency transmission which induces a first current in said first Tesla coil;
    a second Tesla coil that is at least partially disposed in said second conically shaped transmission coil that receives said second multi-frequency transmission which induces a second current in said second Tesla coil;
    a first antenna that transmits a first electromagnetic field signal in response to said first current induced in said first Tesla coil;
    a second antenna that transmits a second electromagnetic field signal in response to said second current induced in said second Tesla coil.

3. The electromagnetic generator of claim 2 further comprising:
    first gaseous emission tubes connected between said first Tesla coil and said first antenna that emit visible light in response to said first current induced in said first Tesla coil;
    second gaseous emission tubes connected between said second Tesla coil and said second antenna that emit visible light in response to said second current induced in said second Tesla coil.

4. The electromagnetic generator of claim 3 further comprising:
    a controller connected to said alternating current input that controls operation of said electromagnetic generator.

* * * * *